US011285245B2

(12) United States Patent
McFarland et al.

(10) Patent No.: US 11,285,245 B2
(45) Date of Patent: Mar. 29, 2022

(54) MEDICAL DEVICES INCLUDING FUNCTIONALIZED POLYMERS AND RELATED METHODS

(71) Applicant: C.R. BARD, INC., Murray Hill, NJ (US)

(72) Inventors: Todd McFarland, Larue, TX (US); James Freasier, Salt Lake City, UT (US); Aaron Francis, Salt Lake City, UT (US); Colton Jackson, Cottonwood Heights, UT (US)

(73) Assignee: C.R. Bard, Inc., Murray Hill, NJ (US)

( * ) Notice: Subject to any disclaimer, the term of this patent is extended or adjusted under 35 U.S.C. 154(b) by 151 days.

(21) Appl. No.: 16/270,343

(22) Filed: Feb. 7, 2019

(65) Prior Publication Data

US 2019/0247550 A1 Aug. 15, 2019

Related U.S. Application Data

(60) Provisional application No. 62/628,668, filed on Feb. 9, 2018.

(51) Int. Cl.
*A61L 31/12* (2006.01)
*A61L 29/04* (2006.01)
*A61L 29/18* (2006.01)
*A61L 29/06* (2006.01)

(52) U.S. Cl.
CPC .......... *A61L 31/127* (2013.01); *A61L 29/041* (2013.01); *A61L 29/06* (2013.01); *A61L 29/18* (2013.01)

(58) Field of Classification Search
CPC .......... A61L 31/27; A61L 29/04; A61L 29/14; A61L 29/049; B23B 27/32; A61M 25/00
See application file for complete search history.

(56) References Cited

U.S. PATENT DOCUMENTS

| | | | |
|---|---|---|---|
| 2002/0077606 A1 | 6/2002 | Trotta | |
| 2004/0116901 A1* | 6/2004 | Appling | A61L 29/18 604/523 |
| 2006/0134357 A1* | 6/2006 | Godaire | A61L 29/049 428/35.2 |
| 2014/0058045 A1* | 2/2014 | Hermel-Davidock | C08F 8/34 525/327.4 |
| 2015/0258247 A1* | 9/2015 | Rostami | A61L 29/049 604/544 |

* cited by examiner

*Primary Examiner* — Dah-Wei D. Yuan
*Assistant Examiner* — Andrew J Bowman
(74) *Attorney, Agent, or Firm* — Kirton McConkie; Whitney Blair; Kevin Stinger

(57) ABSTRACT

Medical devices that are formed from a polymeric matrix including a first polymer and a functionalized polymer are provided. The medical devices may include a functionalized polymer such as maleic anhydride functionalized polymer. The burst strength and/or the hoop strength of the medical devices including the functionalized polymer may be greater than the burst strength and/or the hoop strength of control medical devices. However, the durometer of the medical devices may be substantially equal to the durometer of the control medical devices. Methods of manufacturing medical devices including a functionalized polymer are also provided.

8 Claims, 8 Drawing Sheets

US 11,285,245 B2

MEDICAL DEVICES INCLUDING FUNCTIONALIZED POLYMERS AND RELATED METHODS

CROSS-REFERENCE TO RELATED APPLICATION

This application claims the benefit of U.S. Provisional Application No. 62/628,668, filed Feb. 9, 2018, and entitled MEDICAL DEVICES INCLUDING FUNCTIONALIZED POLYMERS AND RELATED METHODS, which is incorporated herein in its entirety.

TECHNICAL FIELD

The present disclosure relates generally to medical devices including a functionalized polymer. More specifically, the present disclosure relates to medical devices formed from a polymeric matrix including a first polymer and a maleic anhydride functionalized polymer. Related methods are also disclosed.

BRIEF DESCRIPTION OF THE DRAWINGS

The embodiments disclosed herein will become more fully apparent from the following description and appended claims, taken in conjunction with the accompanying drawings.

DETAILED DESCRIPTION

The components of the embodiments as generally described and illustrated herein can be arranged and designed in a wide variety of different configurations. Thus, the following more detailed description of various embodiments is not intended to limit the scope of the present disclosure, but is merely representative of various embodiments. It will be appreciated that various features are sometimes grouped together in a single embodiment, figure, or description thereof for the purpose of streamlining the disclosure. Many of these features may be used alone and/or in combination with one another.

The various embodiments disclosed herein generally relate to medical devices or appliances (e.g., catheters, balloons, etc.) that are formed from a polymeric matrix or mixture, the polymeric matrix including a first polymer and a functionalized polymer. More specifically, various embodiments relate to medical devices including a functionalized polymer such as maleic anhydride polypropylene (MAPP). In some embodiments, the burst strength and/or the hoop strength of the medical devices including the functionalized polymer may be greater than the burst strength and/or the hoop strength of control medical devices (e.g., medical devices lacking the functionalized polymer). Further, the functionalized polymer may not adversely impact the stiffness of the medical devices. For example, the durometer of the medical devices may be substantially equal to the durometer of the control medical devices. Also disclosed herein are methods of manufacturing medical devices including a functionalized polymer.

The term "functionalized polymer," as used herein, refers to a polymer (i.e., a non-functionalized polymer) wherein one or more chemical groups or moieties have been bound or grafted to the polymer. For example, one or more chemical groups can be bound or grafted to the backbone of the polymer. In such embodiments, the chemical groups or moieties can be referred to as pendant groups. The functionalized polymer may have different chemical, physical, biological, pharmacological, and/or other properties than the non-functionalized polymer. In certain embodiments, the functionalized polymer can also be referred to as a modified polymer.

Figure 1:
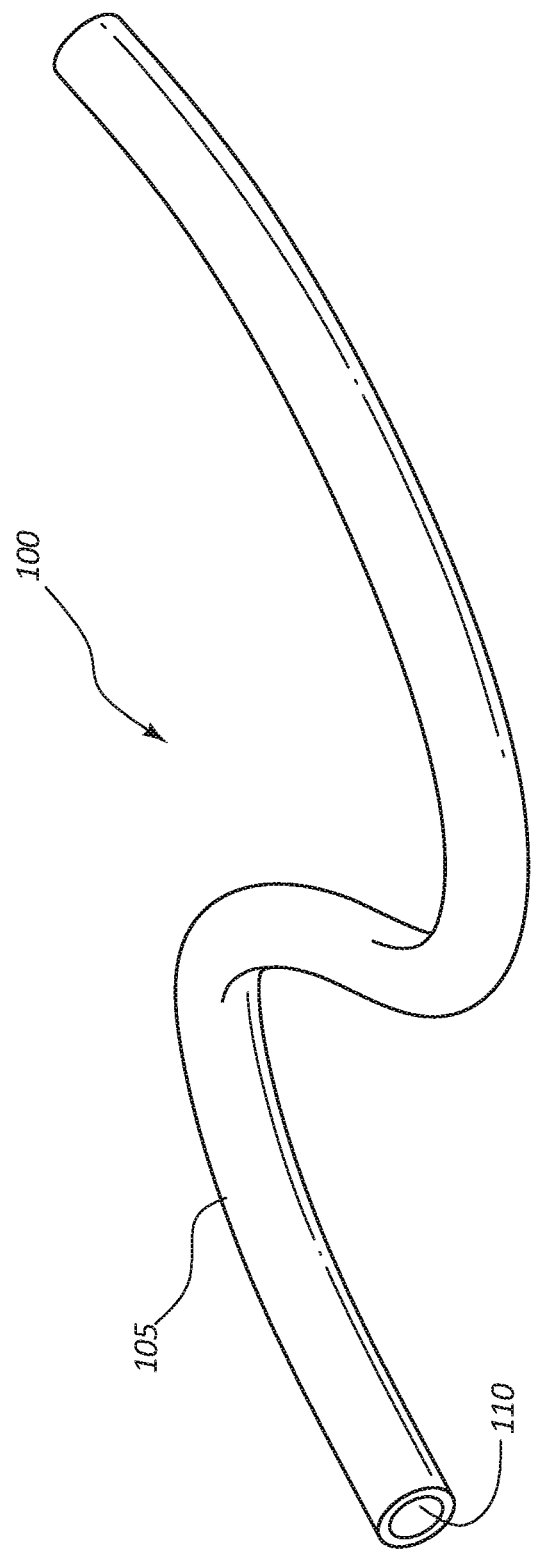
FIG. 1 is a perspective view of an extruded medical device.

FIG. 1 depicts a medical device 100 that includes a first polymer and a functionalized polymer. As shown therein, the medical device 100 may be an extruded medical device. For example, at least a portion of the medical device 100 may be formed by extrusion of a polymeric matrix including a first polymer and a functionalized polymer. In some embodiments, the polymeric matrix includes a substantially uniform distribution of the first polymer and the functionalized polymer such that the first polymer and the functionalized polymer can be distributed throughout the extruded medical device following extrusion of the polymeric matrix.

As shown in FIG. 1, the extruded medical device 100 may include an elongate body 105 formed from a polymeric matrix. The extruded medical device 100 may also include a lumen 110 extending through at least a portion of the elongate body 105. In certain embodiments, the extruded medical device 100 may be a catheter (e.g., a peripheral intravenous line, a central venous line, and a urinary catheter) or a balloon catheter. Other suitable medical devices are also within the scope of this disclosure.

It will further be appreciated that the shape and/or size of the medical device 100 can be varied as desired. For example, various shapes and/or sizes of extrusion dies can be used to form medical devices or structures having particular shapes and/or sizes. Accordingly, it will be understood that the embodiment of FIG. 1 is merely exemplary of one type of extruded medical device.

Various types of polymers (i.e., first polymers) can be used in the polymeric matrix. For example, in some embodiments, the first polymer may include a polyurethane, a polyether block amide (e.g., PEBAX®), a polyamide (nylon), and/or combinations or derivatives thereof. Other types of polymers can also be used.

In certain embodiments, the first polymer may be a nitrogen containing polymer. Stated another way, the first polymer may include nitrogen. The first polymer can also include a nitrogen bound to at least one hydrogen. For example, in some of such embodiments the first polymer comprises a polymer having an amine group, such as a secondary amine group. In particular embodiments, the first polymer may be a polyurethane. In other embodiments, the first polymer may be a polyether block amide. In yet other embodiments, the first polymer may be a polyamide (nylon). Exemplary first polymers that can be used include, but are not limited to, PEBAX®. Other suitable first polymers are also within the scope of this disclosure.

In embodiments wherein the first polymer includes a polyurethane, the polyurethane may be formed from an isocyanate, a polyol, and a chain extender. Exemplary isocyanates that can be used include, but are not limited to, aliphatic H12MDI, dicyclohexylmethane-4,4'-diisocyanate, aromatic methylene diphenyl diisocyanate (MDI), and/or combinations or derivatives thereof. Other suitable isocyanates are also within the scope of this disclosure. Exemplary polyols that can be used include, but are not limited to, polyether, polytetramethylene oxide (PTMO), polycarbonate dial, poly(1,6-hexanediol) carbonate (e.g., having a molecular weight of between about 1000 g/mol and about 3000 g/mol), and/or combinations or derivatives thereof. Other suitable polyols are also within the scope of this disclosure. Exemplary chain extenders that can be used include, but are not limited to, 1,4-butanediol, 1,6-hexanediol, and/or combinations or derivatives thereof. Other suitable chain extenders are also within the scope of this disclosure. Aliphatic and/or aromatic polyurethanes can be used.

As previously stated, the polymeric matrix can also include a functionalized polymer that can impart one or more properties to the polymeric matrix (or a device made therefrom). Various types of polymers can be functionalized or modified in accordance with the present disclosure. For example, in some embodiments, the functionalized polymer can include a polyolefin (e.g., a polymer produced from an alkene). In particular embodiments, the functionalized polymer includes at least one of polyethylene (PE; e.g., high-density polyethylene (HOPE), low-density polyethylene (LOPE), and linear low-density polyethylene (LLDPE)), polypropylene (PP) (e.g., polypropylene homopolymer and polypropylene copolymer), polyamide (PA), polyethylene terephthalate (PET), syndiotactic polystyrene (SPS), polyphenyl ether (PPE), ethylene-vinyl acetate (EVA), polyethylene glycol (PEG) or polyethylene oxide (POE), ethylene propylene diene (EPDM), ethylene butyl acrylate (EBA), cellulose, hydrogenated poly-isoprene/butadiene (SEEPS), and/or combinations or derivatives thereof. In further embodiments, the functionalized polymer may be a thermoplastic polymer. Other suitable polymers are also within the scope of this disclosure. For example, the functionalized polymer may be a maleic anhydride polypropylene (MAPP). The functionalized polymer also includes one or more functional groups bound or grafted to the polymer. As set forth above, a functional group may alter or modify chemical, physical, biological, pharmacological, and/or other properties of the polymer. For example, the functional group may increase the hydrophilicity of the polymer. In another example, the functional group may be charged such that the functional group renders the polymer ionic. Exemplary functional groups that can be used include, but are not limited to, chemical groups or moieties including an acid anhydride of an acid, such as an acid anhydride of a carboxylic acid, a dicarboxylic acid, etc. In various embodiments, the functional group may include a maleic anhydride, a styrene, an acrylic acid, a vinyl chloride, a vinyl acetate glycidyl methacrylate, a methacrylic acid, a vinyl silane, a butyl acrylate, a hydroxyethyl acrylate, and/or combinations or derivatives thereof. Other suitable functional groups are also within the scope of this disclosure.

The amount of functionalized polymer in the polymeric matrix can vary. In some embodiments, the weight-to-weight ratio of the functionalized polymer in the polymeric matrix may be between about 0.25 wt % and about 5 wt %, between about 0.5 wt % and about 2 wt %, between about 1 wt % and about 1.5 wt %, or another suitable percentage.

In certain embodiments, the degree of functionalization of the functionalized polymer may be between about 0.5 wt % and about 5 wt %, between about 0.5 wt % and about 2.5 wt %, between about 1 wt % and about 2 wt %, between about 1 wt % and about 1.8 wt %, or another suitable percentage. Generally, the degree of functionalization is the amount of the functional group (e.g., maleic anhydride) added to the polymeric backbone (e.g., the polymer to be functionalized—such as polypropylene).

Mixing of a first polymer with a functionalized polymer to generate a polymeric matrix for use in forming a medical device can enhance or increase the burst strength and/or the hoop strength of the medical device in comparison to a control medical device formed from a control polymeric matrix including the first polymer but lacking the functionalized polymer. For example, addition of MAPP to a polyether-based thermoplastic urethane (TPU), such as QUADRAFLEX™, to generate a polymeric matrix for use in forming at least a portion of an extruded medical device can increase the burst strength and/or the hoop strength of the extruded medical device in comparison to a control medical device formed from a control polymeric matrix including QUADRAFLEX™ but lacking MAPP. Without being bound by any one particular theory, mixing of the first polymer with the functionalized polymer to generate the polymeric matrix can allow for the formation of hydrogen bonds between the first polymer and the functionalized polymer (see, e.g., FIG. 2). Such hydrogen bonds can enhance the burst strength and/or the hoop strength of a medical device formed from the polymeric matrix.

In an extruded medical device including a first polymer and a functionalized polymer, such as a catheter, the hydrogen bonding may form temporary networks in the hoop direction of the medical device. As is known to the skilled artisan, hydrogen bonding can be reversible. Accordingly, temporary networks formed by hydrogen bonding may allow for reversible and/or dynamic reinforcement of the medical device (e.g., while the medical device is under load). For example, if the medical device is a catheter, the temporary networks can reversibly and/or dynamically reinforce the catheter upon injection of a substance (e.g., a fluid) through the catheter.

Incorporation of the functionalized polymer into the polymeric matrix may not adversely impact the stiffness of the medical device. For example, in various embodiments, the durometer of the medical device or at least a portion of the medical device may be between about 78 A and about 102 A, between about 88 A and about 98 A, between about 91 A and about 95 A, about 93 A, or another suitable durometer. In some embodiments, the burst strength of the medical device or at least a portion of the medical device may be increased by at least about 25 psi, at least about 50 psi, at least about 75 psi, or at least about 100 psi when compared to the control medical device. Furthermore, as the burst strength of the medical device is increased, the durometer of the medical device may remain within about ±5 A, within about ±4 A, within about ±3 A, within about ±2 A, within about ±1 A, or within another suitable durometer range of the durometer of the control medical device.

One or more additional components can also be added to the polymeric matrix. For example, the polymeric matrix of the extruded medical device may further include a radiopaque agent or radiopacifier. Exemplary radiopaque agents include, but are not limited to, barium sulfate, bismuth trioxide, bismuth subcarbonate, bismuth oxychloride, tungsten, and/or combinations or derivatives thereof. Other suitable radiopaque agents are also within the scope of this disclosure. In some embodiments, the radiopaque agent may include barium sulfate. In various embodiments, the radiopaque agent may include bismuth trioxide. In certain embodiments, the radiopaque agent may include bismuth subcarbonate. In further embodiments, the radiopaque agent may include bismuth oxychloride. In other embodiments, the radiopaque agent may include tungsten. The weight-to-weight ratio of the radiopaque agent in the polymeric matrix may be between about 10% and about 40%, between about 25% and about 35%, or another suitable percentage.

The extruded medical device may further include processing aids (e.g., standard processing aids), waxes, antioxidants, and/or colorants. Exemplary antioxidants include, but are not limited to, IRGANOX® 1010, butylated hydroxytoluene (BHT), and/or combinations or derivatives thereof. Other suitable antioxidants are also within the scope of this disclosure. An exemplary wax includes ethylene bis-stearamide (EBS). Other suitable waxes are also within the scope of this disclosure.

In particular embodiments, the medical device or the extruded medical device may be formed from a polymeric matrix including a polyurethane. For example, the medical device may be formed from an aliphatic or an aromatic polyurethane. In some embodiments, the durometer of at least a portion of the medical device may be between about 78 A and about 102 A, between about 88 A and about 98 A, between about 91 A and about 95 A, about 93 A, or another suitable durometer. The medical device may include one or more of standard processing aids, waxes, antioxidants, and/or colorants. In further embodiments, the medical device may include barium sulfate (e.g., as a radiopaque agent). The weight-to-weight ratio of the barium sulfate in the polymeric matrix may be between about 10% and about 40% or between about 25% and about 35%. In some embodiments, the medical device may include MAPP. In some embodiments, the weight-to-weight ratio of the MAPP in the polymeric matrix may be between about 0.5 wt % and about 2 wt %. In some embodiments, the weight-to-weight ratio of the MAPP in the polymeric matrix may be between about 0.5 wt % and about 8 wt %. Furthermore, the degree of functionalization of the MAPP may be between about 0.5 wt % and about 5 wt % or between about 1 wt % and about 1.8 wt %.

Another aspect of the disclosure relates to methods of manufacturing or making medical devices. In certain embodiments, the methods may include obtaining or forming a polymeric matrix including a first polymer and a functionalized polymer. The methods may further include extruding the polymeric matrix to form at least a portion of a medical device. The medical device may include an elongate body and a lumen extending through at least a portion of the elongate body (see, e.g., FIG. 1).

In some embodiments, obtaining the polymeric matrix may include mixing the first polymer and the functionalized polymer (e.g., to form the polymeric matrix). Furthermore, one or more hydrogen bonds may be formed between the first polymer and the functionalized polymer.

Figure 2:
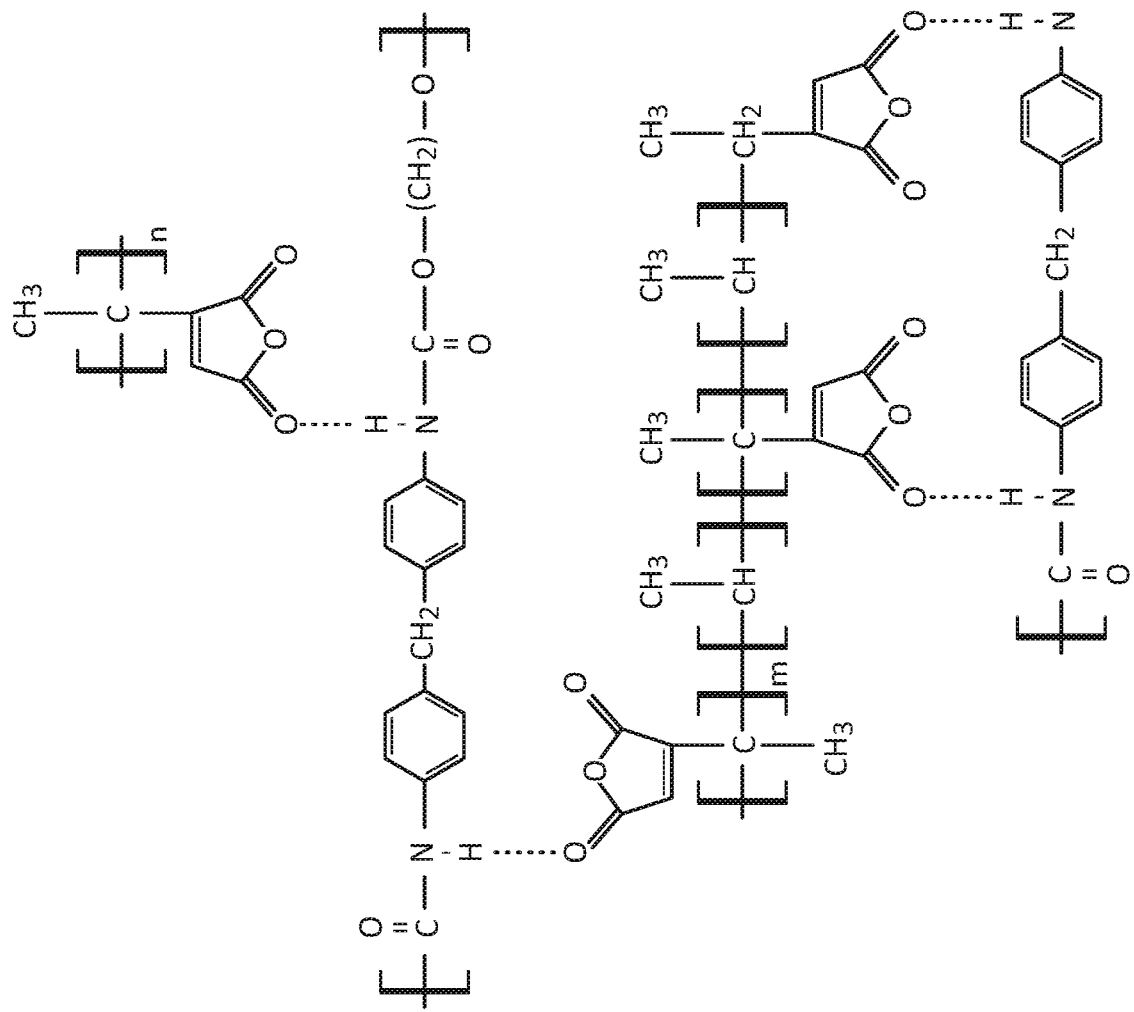
FIG. 2 is a chemical structure showing hydrogen bond formation in a polymeric matrix used to form a medical device.

In some embodiments, the medical device or the portion of the medical device may be formed from a polymeric matrix including MAPP and a first polymer that is a nitrogen containing polymer. Furthermore, the methods of manufacturing such a medical device (or the portion of the medical device) may further include forming one or more hydrogen bonds between the MAPP and the nitrogen containing first polymer. As shown in FIG. 2, hydrogen bonds (dashed lines) can be formed between the nitrogen containing first polymer and the MAPP.

In certain embodiments, the methods of manufacturing the medical devices may increase the burst strength and/or the hoop strength of an extruded medical device while maintaining or substantially maintaining the durometer of the extruded medical device. For example, the durometer of the medical device can be within about 5 A of the durometer of a control medical device formed by extruding a control polymeric matrix including the first polymer but lacking the functionalized polymer, and forming the control polymeric matrix into at least a portion of the control medical device. In various embodiments, the durometer of the medical device may be within about ±5 A, within about ±4 A, within about ±3 A, within about ±2 A, within about ±1 A, or within another suitable durometer range of the durometer of the control medical device. In certain embodiments, the burst strength of the medical device can be greater than the burst strength of the control medical device.

Another aspect of the disclosure relates to methods of increasing the burst strength of an extruded medical device. The methods may include obtaining a polymeric matrix and extruding the polymeric matrix to form at least a portion of a medical device. The durometer of at least a portion of the extruded medical device may be between about 78 A and about 102 A, between about 88 A and about 98 A, between about 91 A and about 95 A, about 93 A, or another suitable durometer. Furthermore, the burst strength of the portion of the medical device may be increased by at least about 25 psi, at least about 50 psi, at least about 75 psi, or at least about 100 psi when compared to a control medical device.

In some embodiments, the durometer of the extruded medical device may b e within about ±5 A, within about ±4 A, within about ±3 A, within about ±2 A, within about ±1 A, or within another suitable durometer range of the durometer of a control medical device. As can be appreciated, additional methods and/or method steps can be derived from the present disclosure.

EXAMPLES

To further illustrate these embodiments, the following examples are provided. These examples are not intended to limit the scope of the claimed invention, which should be determined solely on the basis of the attached claims.

Example 1

100 pounds of base TPU was obtained without colorants or radiopaque agents. Radiopaque agents were blended into the TPU to generate the following four groups of resin (25 pounds each): (A) barium sulfate, (B) barium sulfate and functionalized polypropylene (PP), (C) barium sulfate nanoparticles, or (D) bismuth oxychloride (bisoxy). Group B included 1.25% MAPP, wherein the degree of functionalization of the MAPP was about 1.8 wt % maleic anhydride content. Groups A, C, and D were control groups. Group B was formed according to the present disclosure. The resins were then extruded and cut into 100 catheter shaft tubing samples.

Figure 3B:
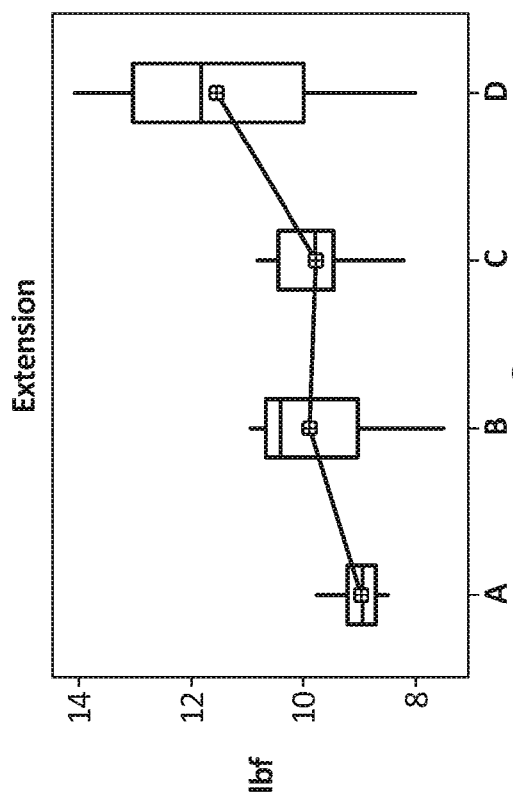
FIG. 3B is a graph depicting extension for the compositions of Groups A-D.
Figure 3A:
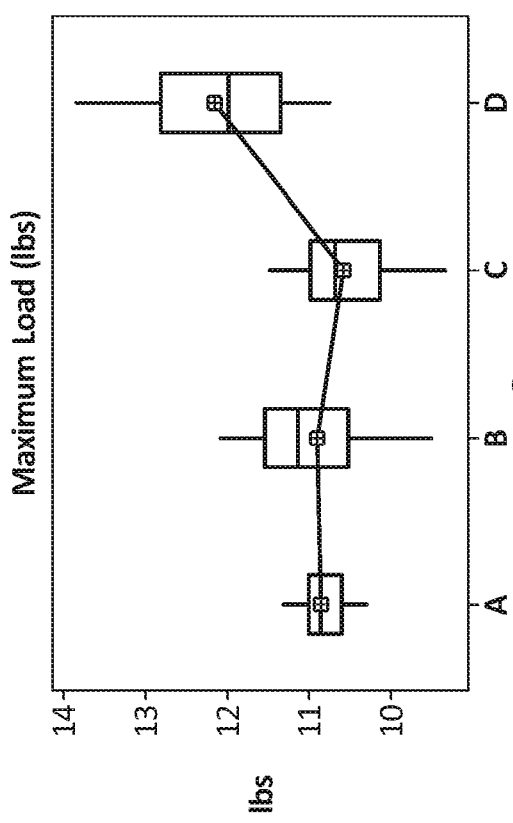
FIG. 3A is a graph depicting maximum loads for the compositions of Groups A-D.
Figure 3C:
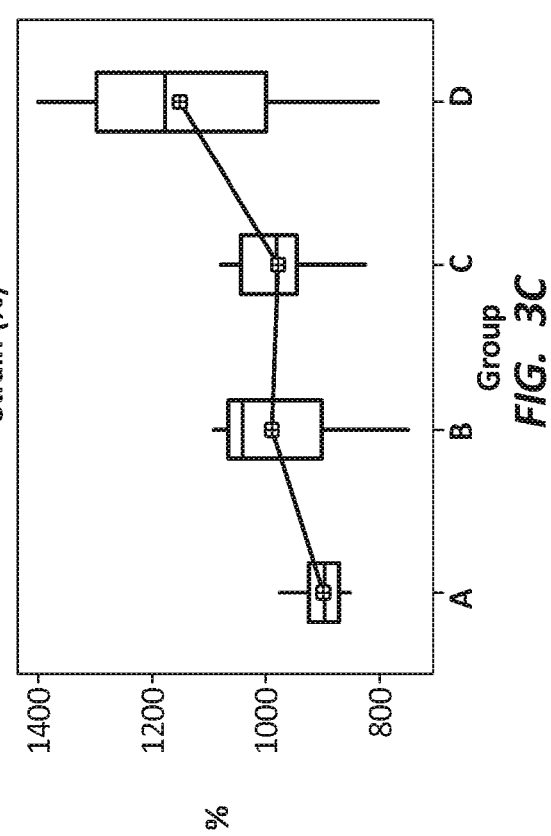
FIG. 3C is a graph depicting strain for the compositions of Groups A-D.

A first test was conducted to assess the tensile strength of catheter shaft tubing samples from each group at their weakest section and to measure the ultimate elongation of catheter shaft tubing sample from each group. This test was administered after the catheter shaft tubing samples had completed a minimum two hour soak in saline at 37° C. Catheter shaft tubing samples from Groups A-C exhibited tensile strengths that were relatively comparable, while tensile strengths of catheter shaft tubing samples from Group D were slightly higher (see FIGS. 3A-3C). Tensile strength testing can include pulling longitudinally on a structure until the structure breaks. As shown, functionalized PP catheters (Group B) did not generally exhibit stronger or negative mechanical properties in the longitudinal (i.e., extruded) direction, but the functionalized PP catheters (Group B) showed large increases in mechanical properties in the transverse direction (i.e., increased hoop strength).

Figure 4A:
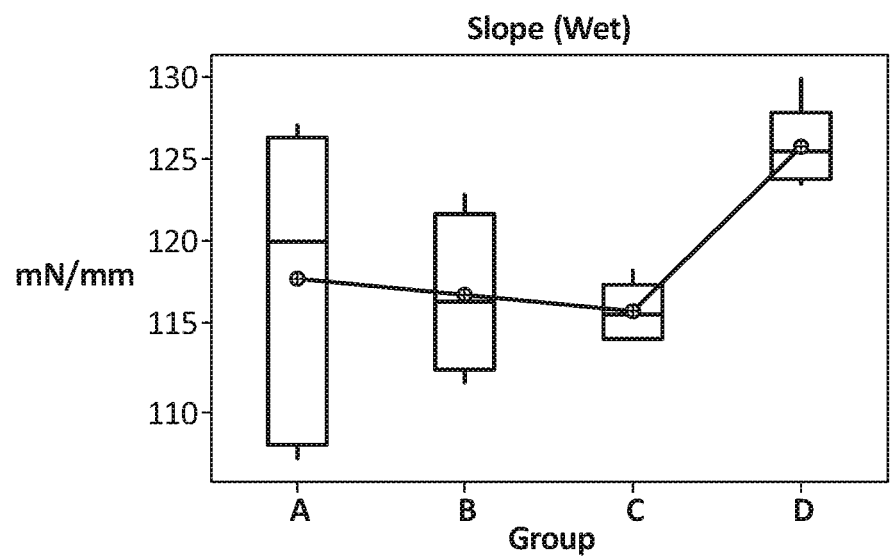
FIG. 4A is a graph depicting slope (wet) for the compositions of Groups A-D.
Figure 4B:
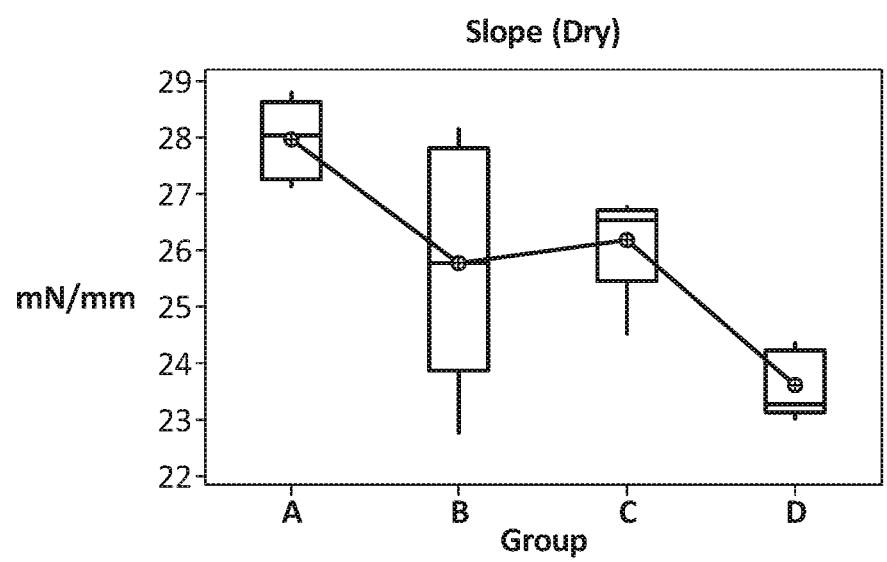
FIG. 4B is a graph depicting slope (dry) for the compositions of Groups A-D.

A second test was conducted to characterize stiffness of catheter shaft tubing samples from each group at both their distal and middle sections using a cantilever bend technique. Testing was performed on dry catheter shaft tubing samples and then repeated on catheter shaft tubing samples soaked in deionized water (DI water) at 37° C. for greater than 2 hours (i.e., wet catheter shaft tubing samples) (see FIGS. 4A and 4B). The second test indicated that the stiffness of the catheter shaft tubing samples from control Group D was negatively impacted, while each of Groups A-C exhibited an acceptable stiffness.

Figure 5:
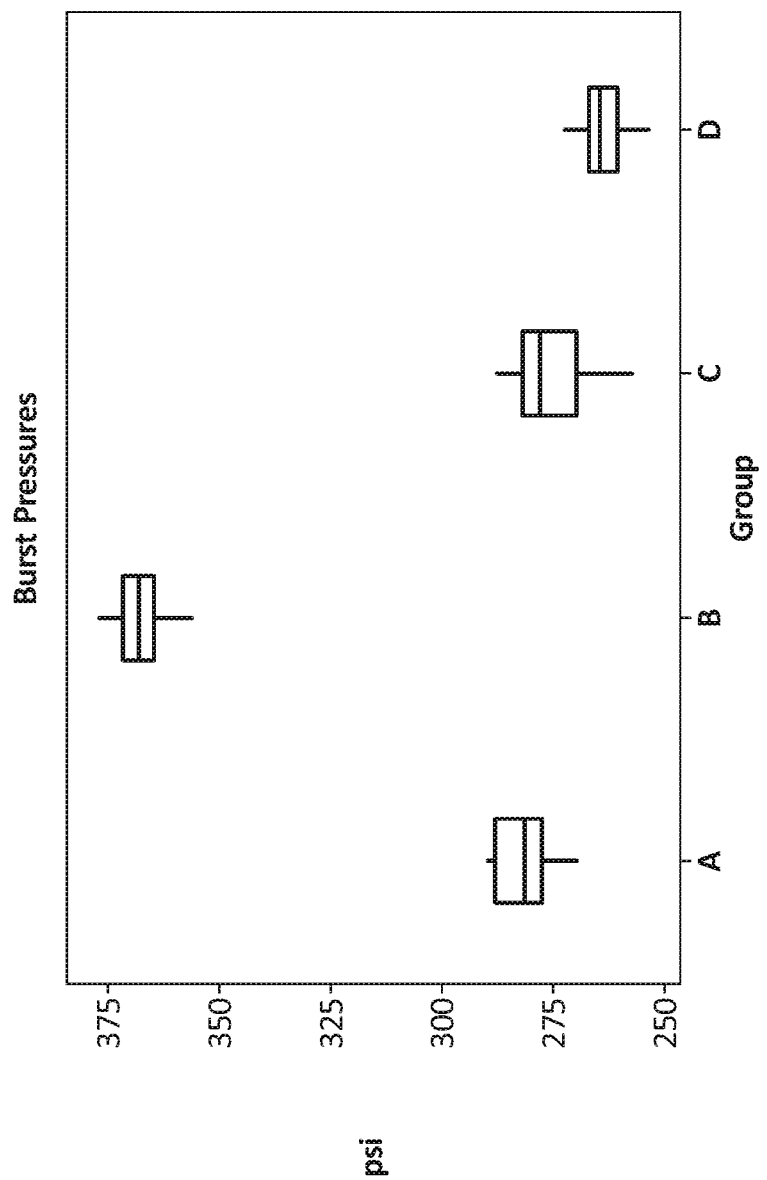
FIG. 5 is a graph depicting burst pressures (psi) for the compositions of Groups A-D.

Catheter burst testing was performed to determine whether the catheter shaft tubing samples were able to withstand pressures at or above that which they may experience under normal use conditions. The results from catheter burst testing indicated that walls of the catheter shaft tubing samples including barium sulfate and functionalized PP (Group B) withstood higher internal air pressure than the catheter shaft tubing samples from control Groups A, C, and D (see Table 1 and FIG. 5).

TABLE 1

Air Burst Results*

|  | Group A | Group B | Group C | Group D |
| --- | --- | --- | --- | --- |
| Description | Barium sulfate | Barium sulfate/ functionalized PP | Barium sulfate nanoparticles | Bisoxy |
| Average | 281.8 psi | 367.9 psi | 276.9 psi | 263.7 psi |
| Std. Dev. | 5.967 | 5.749 | 8.173 | 4.884 |
| Anderson-Darling normality test (p-value)** | 0.651 | 0.755 | 0.327 | 0.804 |

*N = 15 for each group
**Distribution is treated as normal for p-values > 0.05

Figure 6B:
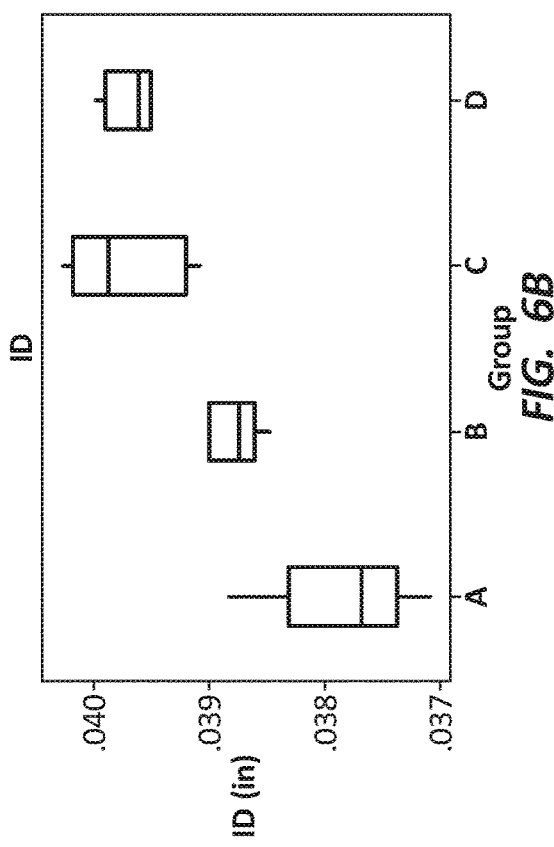
FIG. 6B is a graph depicting the inner diameter (ID) of catheters formed from the compositions of Groups A-D.
Figure 6A:
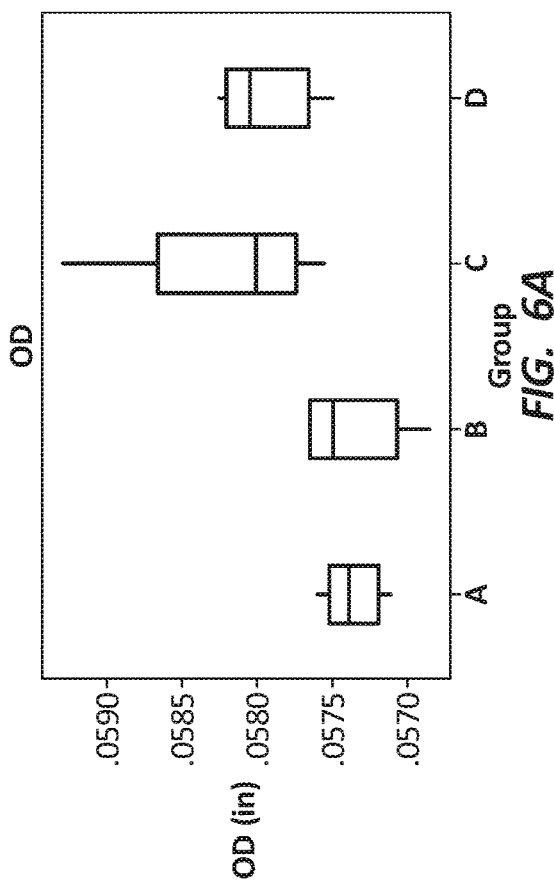
FIG. 6A is a graph depicting the outer diameter (OD) of catheters formed from the compositions of Groups A-D.
Figure 6C:
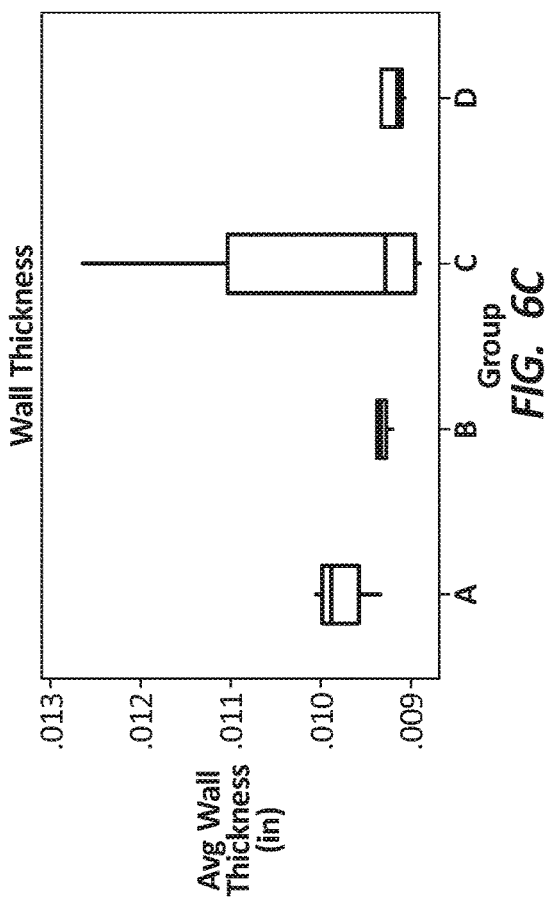
FIG. 6C is a graph depicting the wall thickness of catheters formed from the compositions of Groups A-D.

Extrusion dimensions (distal end) were also obtained. It was determined that the catheter shaft tubing samples from Group B (barium sulfate and functionalized PP) did not exhibit unusual dimensional features. Catheter shaft tubing samples from control Group C (barium sulfate nanoparticles) were the most significantly dimensionally different of the four groups (see FIGS. 6A-6C). Catheter shaft tubing samples from control Group D (bisoxy) were visually different in contrast value from the other extrusions.

Example 2

A multivariable quadratic screening and optimization study was designed around the polyether-based TPU, QUADRAFLEX™ (the "screen"). The screen was conducted with various amounts of MAPP additive, as provided in Table 2 (Groups X-, Y-, and Z-Test). Also, in the Group Y-Test, two different batches of maleic anhydride (MA) were used (Batches 2 and 4).

TABLE 2

Test Parameters of QUADRAFLEX ™ MAPP screen

|  | Group | | |
| --- | --- | --- | --- |
|  | X-Test | Y-Test | Z-Test |
| Durometer | 88 | 93 | 96 |
| Isocyanate Index | 1.0 | 1.05 | 1.1 |
| Barium sulfate (w/w %) | 25% | 30% | 35% |
| Colorant content | None | Half | Full |
| MAPP compounding (w/w)% | 0.5% | 1.25% | 2% |
| MA (degree of functionalization) | 1 wt % (Batch 1) | 1.5 wt % (Batch 2) 0.8 wt % (Batch 4) | 1.8 wt % (Batch 3) |

QUADRAFLEX™ resin was compounded with colorant, barium sulfate, and MAPP additive and then extruded (4 Fr S/L with no bump or taper). Control extrusions were done without MAPP additive for comparison, as provided in Table 3 (Groups X-, Y-, and Z-Control). The finding of the screen was that each of Groups X-, Y-, and Z-Test was processable and extrusions were successfully made to specification.

TABLE 3

Control Parameters of QUADRAFLEX ™ MAPP screen

|  | Group | | |
| --- | --- | --- | --- |
|  | X-Control | Y-Control | Z-Control |
| Durometer | 88 | 93 | 96 |
| Isocyanate Index | 1.0 | 1.05 | 1.1 |
| Barium sulfate (w/w %) | 25% | 30% | 35% |
| Colorant content | None | Half | Full |
| MAPP compounding (w/w)% | 0% | 0% | 0% |

Figure 7:
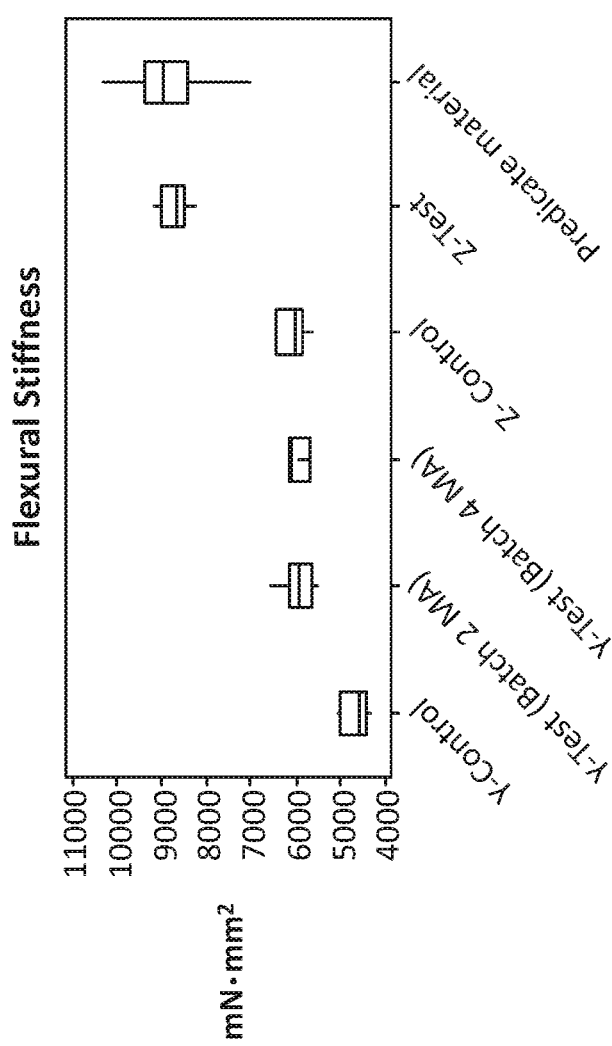
FIG. 7 is a box plot of flexural stiffness.

Flexural stiffness of the extrusions was tested (see Table 4) and compared to a predicate material (an aromatic polyurethane lacking MAPP; 4 Fr D/L-R84438-03). The flexural stiffness data of the predicate material was not normal, accordingly medians were compared. All groups of extrusions (Test and Control) were shown to be statistically lower in flexural stiffness than that of the predicate material except for Group Z-Test, which was shown to be statistically the same (see FIG. 7). As indicated, extrusions having increased burst strength were procured (i.e., Y-Control, Z-Control, Y-Test (Batch 2 MA), and Y-Test (Batch 4 MA)) without negatively affecting stiffness (e.g., without increasing stiffness). Indeed, the stiffness of the indicated extrusions was lower than in the predicate material.

TABLE 4

Flexural Stiffness Comparisons

Flexural Stiffness (mN · mm$^2$)

| Test Material | Average/Median | Standard Deviation | AD Normality (p-value) | Test of Equivalence (p-value) | Results |
|---|---|---|---|---|---|
| Y-Control | 4663/4596 | 288 | 0.563 | 0.0001 | Statistically lower than predicate material |
| Z-Control | 6081/6038 | 307 | 0.518 | 0.0001 | |
| Y-Test (Batch 2 MA) | 5938/5935 | 351 | 0.303 | 0.0001 | |
| Y-Test (Batch 4 MA) | 5896/6103 | 509 | <0.005 | 0.0001 | |
| Z-Test | 8710/8672 | 321 | 0.895 | 0.2745 | Median is statistically the same as predicate material |
| Predicate material | 8847/8991 | 795.8 | 0.032 | N/A | N/A |

\* AD (Anderson Darling), p-value > 0.05 is considered to have a normal distribution. Test of equivalence is based on 2-sample t-test for normally distributed data. For non-parametric data (AD p-value < 0.05), a Mood's Median test was used to test for equivalence.

Hydraulic burst leak testing (HBLT) was also performed to measure the effects of MAPP additive on hoop strength. MAPP additive was found to increase burst values for all groups (see Table 5). Additionally, all Group Y-Test samples did not burst completely and only failed from a slight pressure drop due to a compliance change stopping the test.

TABLE 5

Burst Value Comparisons

| Group | Control Average (PSIG) | MAPP additive Average (PSIG) | Percent change |
|---|---|---|---|
| Y-Test (Batch 2 MA) | 287.6 | 316.3 | 10.0% |
| Y-Test (Batch 4 MA) | 287.6 | 335.4 | 16.6% |
| Z-Test | 321.1 | 389.1 | 21.2% |

Figure 8:
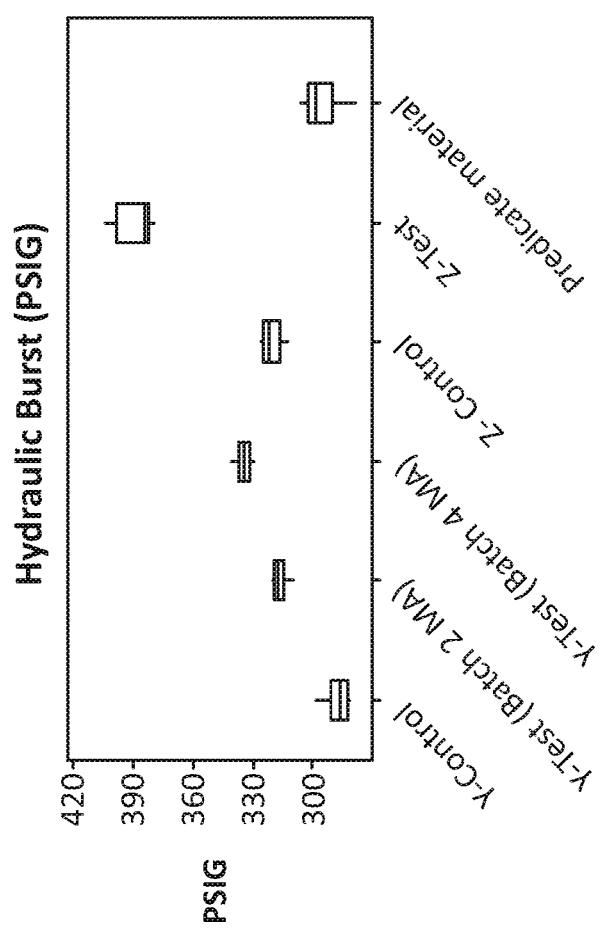
FIG. 8 is a box plot of hydraulic burst testing results.

Additionally, this burst data was compared to the predicate material data and it was found that Groups Y-(Batches 2 and 4) and Z-Test had significantly higher medians than the predicate material (see Table 6 and FIG. 8). As indicated, the burst values of the test extrusions were generally higher than the burst values of their respective control extrusions.

TABLE 6

Burst Value Comparisons to Predicate Material Data

Burst (Psig)

| Test Material | Average/Median | Standard Deviation | AD Normality (p-value) | Test of Equivalence (p-value) | Results |
|---|---|---|---|---|---|
| Y-Control | 287.60/286.50 | 5.82 | 0.060 | 0.000 | Statistically lower median than predicate material |
| Z-Control | 321.10/322.00 | 4.51 | 0.232 | 0.000 | Statistically higher median than predicate material |

TABLE 6-continued

Burst Value Comparisons to Predicate Material Data

| | Burst (Psig) | | | | |
|---|---|---|---|---|---|
| Test Material | Average/ Median | Standard Deviation | AD Normality (p-value) | Test of Equivalence (p-value) | Results |
| Y-Test (Batch 2 MA) | 316.30/317.00 | 3.09 | 0.444 | 0.000 | Statistically |
| Y-Test (Batch 4 MA) | 335.40/334.00 | 5.7 | 0.028 | 0.000 | higher |
| Z-Test | 389.10/384.00 | 9.27 | 0.028 | 0.000 | median than predicate material |
| Predicate material | 295.98/299.00 | 7.87 | <0.005 | N/A | N/A |

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially equal" is recited with respect to a feature, it is understood that in further embodiments, the feature can have a precisely equal configuration.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. An extruded medical device comprising:
   an elongate body formed from a polymeric matrix comprising:
      a first polymer, wherein the first polymer is selected from at least one of polyurethane, polyether block amide, or nylon; and
      a maleic anhydride functionalized polymer, wherein the maleic anhydride functionalized polymer is maleic anhydride polypropylene (MAPP), wherein the weight-to-weight ratio of the maleic anhydride functionalized polymer in the polymeric matrix is between 0.5 wt % and 8 wt %, wherein the degree of functionalization of the maleic anhydride functionalized polymer is between about 0.5 wt % and about 5 wt %; and
   a lumen extending through a portion of the elongate body, wherein the burst strength/hoop strength of a portion of the extruded medical device is increased between about 25 psi and about 100 psi when compared to a control extruded medical device lacking the maleic anhydride functionalized polymer.

2. The extruded medical device of claim 1, wherein the first polymer is configured to form hydrogen bonds with the maleic anhydride functionalized polymer.

3. The extruded medical device of claim 1, wherein the extruded medical device is a catheter or a balloon.

4. The extruded medical device of claim 1, wherein the durometer of a portion of the extruded medical device is between about 78 A and about 102 A.

5. The extruded medical device of claim 1, wherein the polymer of the maleic anhydride functionalized polymer is selected from at least one of polyethylene, polypropylene, polyamide, polyethylene terephthalate, syndiotactic polystyrene, polyphenyl ether, ethylene-vinyl acetate, polyethylene glycol, ethylene propylene diene, ethylene butyl acrylate, cellulose, or hydrogenated poly-isoprene/butadiene.

6. The extruded medical device of claim 1, further comprising a radiopaque agent.

7. The extruded medical device of claim 6, wherein the radiopaque agent is selected from at least one of barium sulfate, bismuth trioxide, bismuth subcarbonate, bismuth oxychloride, or tungsten.

8. The extruded medical device of claim 6, wherein the weight-to-weight ratio of the radiopaque agent in the polymeric matrix is between about 10% and about 40%.

* * * * *